United States Patent
Cronauer

(10) Patent No.: US 7,416,407 B2
(45) Date of Patent: Aug. 26, 2008

(54) ORTHODONTIC APPLIANCE WITH EMBEDDED WIRE FOR MOVING TEETH AND METHOD

(76) Inventor: Edward A. Cronauer, 2249 N. University Dr., Pembroke Pines, FL (US) 33024

( * ) Notice: Subject to any disclaimer, the term of this patent is extended or adjusted under 35 U.S.C. 154(b) by 0 days.

(21) Appl. No.: 11/503,591

(22) Filed: Aug. 14, 2006

(65) Prior Publication Data

US 2006/0275730 A1    Dec. 7, 2006

Related U.S. Application Data

(62) Division of application No. 10/160,943, filed on May 31, 2002, now Pat. No. 7,104,790.

(51) Int. Cl.
*A61C 3/00*    (2006.01)
(52) U.S. Cl. .......................................................... 433/6
(58) Field of Classification Search ...................... 433/6, 433/7, 18, 21; 128/861, 862
See application file for complete search history.

(56) References Cited

U.S. PATENT DOCUMENTS

| | | | |
|---|---|---|---|
| 3,478,742 A | | 11/1969 | Bohlmann |
| 3,574,941 A | * | 4/1971 | Ritter ........................... 433/18 |
| 3,827,146 A | * | 8/1974 | Wallshein ...................... 433/7 |
| 3,994,068 A | | 11/1976 | Goshgarian |
| 4,026,023 A | * | 5/1977 | Fisher ............................ 433/7 |
| 4,054,996 A | * | 10/1977 | Wallshein ...................... 433/7 |
| 4,055,895 A | | 11/1977 | Huge |
| 4,299,568 A | | 11/1981 | Crowley |
| 4,413,978 A | | 11/1983 | Kurz |
| 4,609,349 A | | 9/1986 | Cain |
| 4,793,803 A | | 12/1988 | Martz |
| 4,798,534 A | | 1/1989 | Breads |
| 4,799,500 A | * | 1/1989 | Newbury ..................... 128/859 |
| 4,799,884 A | | 1/1989 | Bergersen |
| 5,194,003 A | * | 3/1993 | Garay et al. ................. 433/215 |
| 5,203,695 A | | 4/1993 | Bergerson |
| 5,310,340 A | | 5/1994 | Zedda |
| 5,536,169 A | | 7/1996 | Yousefain |
| 5,607,300 A | | 3/1997 | Tepper |

(Continued)

*Primary Examiner*—Ralph A. Lewis
(74) *Attorney, Agent, or Firm*—Christopher & Weisberg, P.A.

(57) ABSTRACT

A generally horseshoe shaped clear flexible resilient plastic wire-imbedded orthodontic appliance is made with a plastic portion with contours on the lingual side and on the labial side, wherein the contours snugly cover the patient's teeth so that the appliance remains in place. One or more flexible wires are imbedded within the lingual side of the plastic portion from the left molar area to the right molar area of the plastic portion, whereby the wires apply force on the lingual side of the patient's bite. The appliance is formed by obtaining a plaster cast of the patient's teeth and gums, removing plaster teeth from the plaster cast of the gums, reattaching the plaster teeth to the plaster cast of the gums to form a cast of proper bite alignment, attaching one or more wires to the labial surface of the aligned plaster teeth so the wires become imbedded within thermosetting plastic placed over the cast, putting the cast in a thermosetting plastic molding machine, inserting thermosetting plastic in the machine, and heating the thermosetting plastic around the cast of the proper bite alignment, so the wires are imbedded within the formed appliance after the thermosetting plastic cools. A series of appliances may be used to shift a patient's bite to proper bite orientation.

4 Claims, 3 Drawing Sheets

U.S. PATENT DOCUMENTS

| | | |
|---|---|---|
| 5,645,420 A | 7/1997 | Bergersen |
| 5,836,761 A | 11/1998 | Belvedere et al. |
| 5,876,199 A | 3/1999 | Bergersen |
| 5,879,155 A | 3/1999 | Kittelsen |
| 5,975,893 A | 11/1999 | Chishti et al. |
| 6,604,943 B2 * | 8/2003 | White ............... 433/21 |
| 6,790,036 B2 | 9/2004 | Graham et al. |
| 7,104,790 B2 * | 9/2006 | Cronauer ............ 433/6 |
| D537,945 S * | 3/2007 | White ............... D24/180 |
| D538,434 S * | 3/2007 | White ............... D24/180 |

* cited by examiner

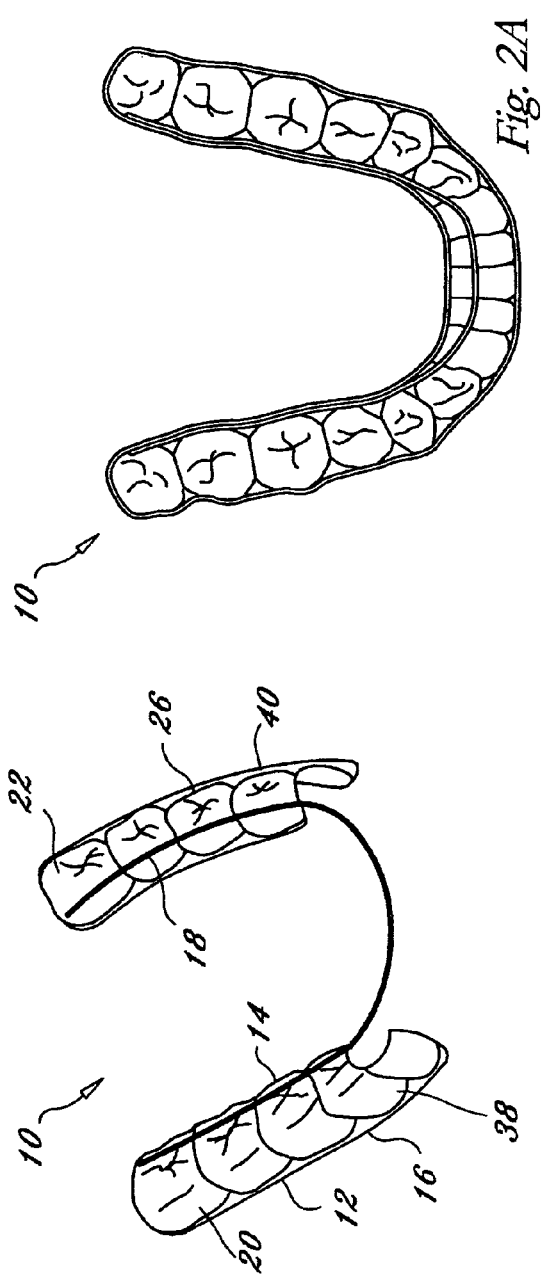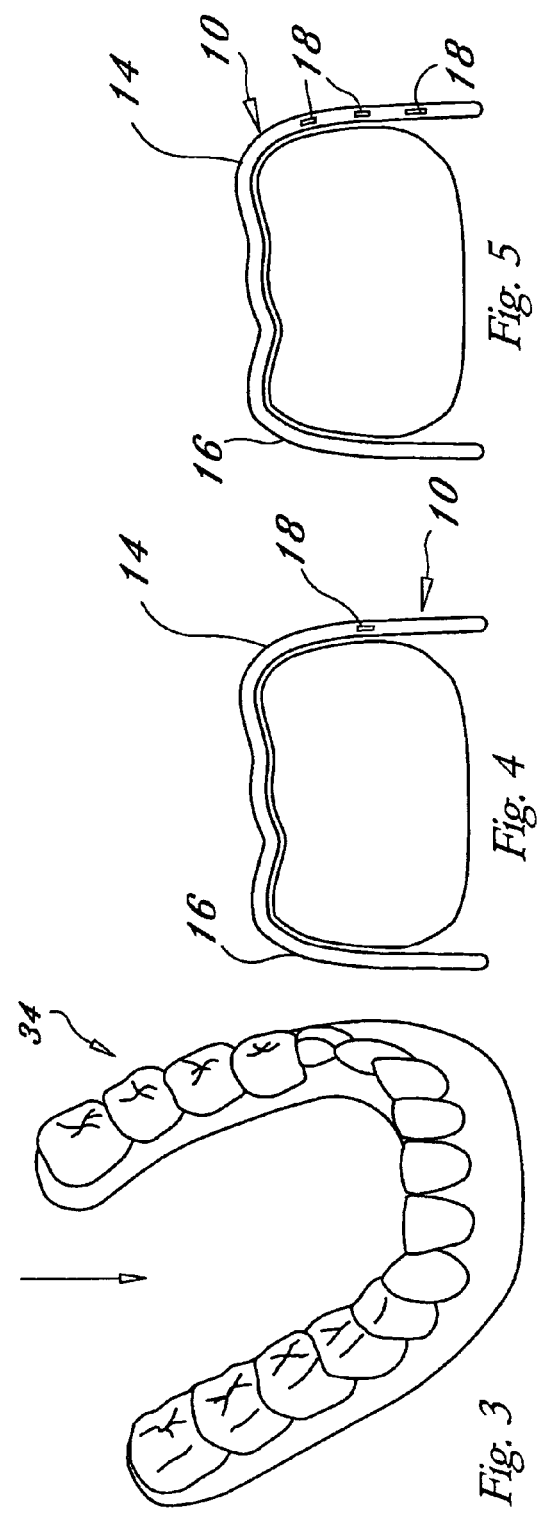

ns with a lingual side, a labial side, a left molar area, a right molar area, a left canine area and a right canine area, and has contours on the lingual side and on the labial side, wherein the contours snugly cover the patient's teeth so that the appliance remains in place over the patient's teeth. One or more flexible wires are imbedded within the lingual side of the plastic portion, extending from the left molar area to the right molar area of the plastic portion, so the wires are able to apply force on the lingual side of the patient's teeth to rapidly correct the orientation of the teeth in the patient's bite.

ORTHODONTIC APPLIANCE WITH EMBEDDED WIRE FOR MOVING TEETH AND METHOD

This application is a Divisional Application of application Ser. No. 10/160,943 filed May 31, 2002, now U.S. Pat. No. 7,104,790 by Edward A. Cronauer, entitled ORTHODONTIC APPLIANCE WITH EMBEDDED WIRE FOR MOVING TEETH AND METHOD, the entirety of all of which is incorporated herein by reference.

BACKGROUND OF THE INVENTION

1. Field of the Invention

Orthodontics is a specialty of dentistry dealing with the correction of a patient's bite and alignment of a patient's teeth. Currently, orthodontic appliances apply forces to the teeth of the patient. These forces physically shift the patient's teeth with precise and complex movements, to conform the teeth to a model created by the orthodontist or a laboratory specifically suited to the purpose.

2. Description of Related Art

Active treatment of the bite historically involved cementing brackets onto the teeth with one or more arch wires attached. While these brackets are unattractive, they have shown that a wire can be used to rapidly move teeth. The present invention relates to the field of orthodontics. In particular, the invention relates to an orthodontic appliance which comprises a wired imbedded in a plastic matrix.

Teeth are generally repositioned by wearing braces, which include brackets, ligatures, O-rings and archwires. Archwires are wires firmly attached to the brackets and are used to exert a force on teeth either on the lingual side or on the labial side. Recently, apparati have been developed which use a flexible thermoplastic that fit entirely over the upper and/or the lower bridge. However, these apparati have only a limited ability to move teeth.

An orthodontic appliance is described in U.S. Pat. No. 5,310,340 to Zedda. In Zedda, the appliance has a base and support element in which a steel wire extends from the base and support element to a synthetic resin bracket cemented to a tooth. Another orthodontic appliance is described in U.S. Pat. No. 5,536,169 to Yousefian. In Yousefian, The appliance includes a plurality of arcurate polymer strips which includes a wire extending through the length of the strips with transverse adjusting segments. The appliance requires a lingual strip and a labial strip of polymer.

An orthodontic retainer is described in U.S. Pat. No. 3,994,068 to Goshgarian. In Goshgarian, the retainer includes loops outside the body of the device for accurate adjustment on the labial side of the teeth. U.S. Pat. No. 4,299,568 to Crowley describes an orthodontic retainer in which wires contact tooth surface, and which includes palatial overlays. U.S. Pat. No. 5,203,695 to Bergersen teaches a device with a wire that has a sharp and jutting bend. Moreover, the wire is bent and otherwise adjusted after the appliance is made and fitted for the patient. U.S. Pat. No. 4,413,978 to Kurz describes a retainer with wire hooks anchoring the retainer to molars, and has a wire cemented to the person's arch. U.S. Pat. No. 5,975,893 to Chishti, et al., teaches a clear plastic orthodontic device fitted over all of the patient's teeth which slowly moves the teeth through a system of plastic appliances. However, Chishti only teaches the inefficient and slow use of force on the patient's teeth that is intrinsic to the resiliency in the plastic that forms the appliance.

The prior art inventions either attach brackets directly to the teeth or comprise a plastic device that slowly moves the teeth around the bridge. Also, prior art devices require clasps for the wire to be attached to the device. Prior art inventions also include devices that are costly and difficult to manufacture. Permanently attached braces are unsightly, inconvenient when eating or speaking and may cause discoloration or even pain to the patient. The speed by which the prior art plastic devices move teeth is limited by the rigidity of the plastic used. Not even modern plastics can provide sufficient force to quickly reorient the alignment of the teeth or the bite of a patient.

A need exists in the field of orthodontic devices for an easy to manufacture device which quickly moves teeth into an orthodontically advantageous orientation. A need also exists for a device that is clear and therefore invisible to others and which is relatively pain free when worn. The need also exists for a device which allows the chewing surface of the front teeth or the labial side of the front teeth to be exposed while the appliance is worn. Moreover, the need also exists for a removable orthodontic device with a wire imbedded in the lingual surface, providing the advantage of a flexible, clear device with the benefit of one or more wires to provide invisible force on the teeth. There is also a need for a succession of these devices incorporating wires, allowing intricate movement of the patient's teeth. Additionally, there is a need for a method for making these devices.

The instant invention has been directed to the effective resolution of the aforementioned shortcomings and to the meeting of the aforementioned needs.

BRIEF SUMMARY OF THE INVENTION

The present invention provides a novel and unique removable appliance that is easy to manufacture and provides more forceful and less obtrusive movement of teeth while the appliance is worn. The present invention provides relatively pain free and rapid movement of a patient's teeth into a proper orientation. In the preferred embodiment, the invention is a generally horseshoe shaped clear flexible resilient plastic wire-imbedded orthodontic appliance for an upper arch or a lower arch of a patient. The appliance includes a plastic portion with a lingual side, a labial side, a left molar area, a right molar area, a left canine area and a right canine area, and has contours on the lingual side and on the labial side, wherein the contours snugly cover the patient's teeth so that the appliance remains in place over the patient's teeth. One or more flexible wires are imbedded within the lingual side of the plastic portion, extending from the left molar area to the right molar area of the plastic portion, so the wires are able to apply force on the lingual side of the patient's teeth to rapidly correct the orientation of the teeth in the patient's bite.

In an alternative embodiment, the plastic portion covers the surface of the patient's teeth from the left rear molar to the right rear molar. Also, the plastic portion may have a first outer section that covers the entire surface of the patient's teeth from approximately the left molars to the left canines, a second outer section that covers the entire surface of the patient's teeth from approximately the right molars to the right canines, and a middle span that covers only the labial side of the patient's teeth approximately between the canines. In this embodiment, the middle span acts as a guide for the force of the wire upon the patient's teeth.

In still another embodiment, the plastic portion has a first outer section that covers the entire surface of the patient's teeth from approximately the left molars to the left canines, and a second outer section that covers the entire surface of the patient's teeth from approximately the right molars to the right canines. Thus, the plastic portion does not touch the patient's teeth approximately between the patient's canines. Also, a plurality of vertically parallel wires may be imbedded within the lingual side of the plastic portion of the appliance. The appliance may also have vertically parallel wires with a length and cross-sectional shape which optimizes the force applied to the patient's teeth. For example, the cross-sectional shape may be rectangular, round, or oval.

The invention is also a method of forming a generally horseshoe shaped clear flexible resilient plastic wire-imbedded orthodontic appliance for an upper bite or a lower bite of a patient. The method generally includes the steps of obtaining a plaster cast of the patient's teeth and gums, removing plaster teeth from the plaster cast of the gums that are appropriate for the formation of proper bite alignment, reattaching the appropriate plaster teeth to the plaster cast of the gums to form a cast of the proper bite alignment, attaching one or more wires to the lingual surface of the plaster teeth so that the wires become imbedded within thermosetting plastic placed over the cast of the proper bite alignment, putting the cast in a thermosetting plastic molding machine and inserting thermosetting plastic in the thermosetting plastic molding machine, and heating the thermosetting plastic around the cast of the proper bite alignment so the wires are imbedded within the thermosetting plastic after the thermosetting plastic cools. In one embodiment, the method includes the steps of removing the appliance from the thermosetting plastic molding machine and trimming the lingual surface of the appliance to form a middle span, wherein the span acts as a guide for the pushing force of the wire on the patient's bite.

Moreover, the invention includes a method of rapidly repositioning teeth from an initial alignment to a proper alignment using a generally horseshoe shaped clear flexible resilient plastic wire-imbedded orthodontic appliance for an upper bite or a lower bite of a patient, comprising the steps of placing a first incremental position adjustment appliance over a patient's teeth, wherein the first appliance has at least one wire imbedded within the lingual side of the first appliance to reposition the teeth from the initial tooth alignment to a first intermediate alignment, successively replacing one or more additional appliances, wherein the additional appliances each have at least one wire imbedded within the lingual side to rapidly reposition the teeth from the first intermediate alignment to successive intermediate alignments and placing a final appliance over a patient's teeth, wherein the final appliance has at least one wire imbedded within the lingual side of the first appliance to reposition the teeth, wherein the final appliance positions the teeth from the last intermediate alignment to a final bite alignment. Alternatively, a plurality of vertically parallel wires is imbedded within the lingual side of the first appliance, the intermediate appliances and the final appliance.

In accordance with these and other objects which will become apparent hereinafter, the instant invention will now be described with particular reference to the accompanying drawings.

BRIEF DESCRIPTION OF THE SEVERAL VIEWS OF THE DRAWINGS

FIG. 2a is a top view of an alternative embodiment of the invention for the lower bridge of a patient.

FIG. 3 is a perspective drawing of an embodiment of the invention for the lower bridge of a patient.

FIG. 4 is a cross sectional view of the preferred embodiment of the invention for the lower bridge before it is placed on a patient.

FIG. 5 is a cross sectional view of an alternative embodiment of the device with several generally parallel wires embedded within the lingual surface of the appliance.

DETAILED DESCRIPTION OF THE INVENTION

Figure 1:
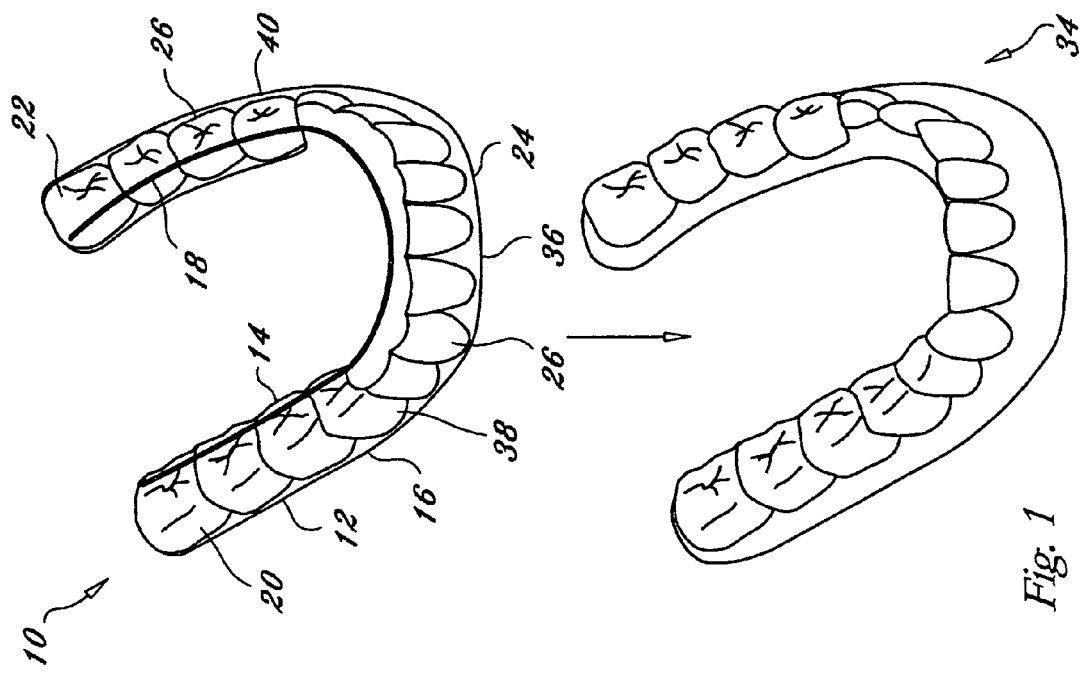
FIG. 1 is a perspective drawing of the preferred embodiment of the invention for the lower bridge of a patient.

Referring now to the drawings and in particular, FIG. 1, the generally horseshoe shaped clear flexible resilient plastic orthodontic appliance for a patient is shown generally at 10. A plastic portion 12 has a lingual side 14 and a labial side 16. Both the lingual side 14 and the labial side 16 have concave contours 26. These contours 26 snugly contact the patient's teeth 34. The contours 26, especially those over the molars, allow the appliance 10 to remain fixed in place over the patient's teeth 34. The contours 26, especially those on the front 36 of the appliance 10, serve the function of guiding the force of the appliance 10 to move the patient's teeth 34 into an advantageous position. On the lingual side 14 of the appliance 10 are one or more flexible wires 18 at least partially embedded within the plastic portion 12. Preferably, the wires 18 are made of a nickel-titanium alloy or stainless steel, although other similar materials which would provide force on the patient's teeth may also be used. It is also preferred that the diameter of the wire be approximately 12 to 18 thousandths of an inch. However, depending upon the force necessary to improve the patient's bite, the wire 18 may be of greater or lesser diameter. The wire 18 may round, oval, square, or some other shape in cross-section which, when used, is advantageous to the patient's bite. Moreover, as shown in FIG. 5, several generally vertically parallel wires 18 may be used.

In the preferred embodiment, a flexible wire 18 extends generally from a left molar area 20 to a right molar area 22 of the plastic portion 12. However, the wire 18 may alternatively extend from left bicuspid area 38 to right bicuspid area 40 of the plastic portion 12, or extend other areas where the force of the wire 18 would help the patient's bite. Thus, when worn by the patient, the wires 18 apply force on the lingual side of the patient's bite. The wire 18 thereby aids in the rapid correction of the orientation of the patient's bite while the appliance 10 is in use. The appliance 10 may be used on the patient's upper jaw or the lower jaw, or for use on both jaws simultaneously.

In the preferred embodiment, as shown in FIG. 1, the plastic portion 12 includes a span 24 which covers the patient's teeth from the left canine area 30 to a right canine area 32. This span 24 also contains contours 26 as described above. As illustrated in FIG. 1, the plastic portion 12 preferably covers the entire front surface of the patient's teeth from the patient's molars approximately to the patient's canines, and the span 24 covers the labial side of the teeth approximately between the canines. Thus the span 24 across the labial side of the patient's teeth acts as a guide for the force of the wire 18. As shown in FIG. 5, multiple parallel wires 18 may be used on the labial side of the appliance 10, thereby increasing the moving force on the patient's teeth. To precisely apply force on the teeth, wires of varying strength, diameter and cross sectional shape may be used. For example, although wires 18 with rectangular cross-section are shown in FIG. 4, round or oval wires 18 may be used.

Figure 2:
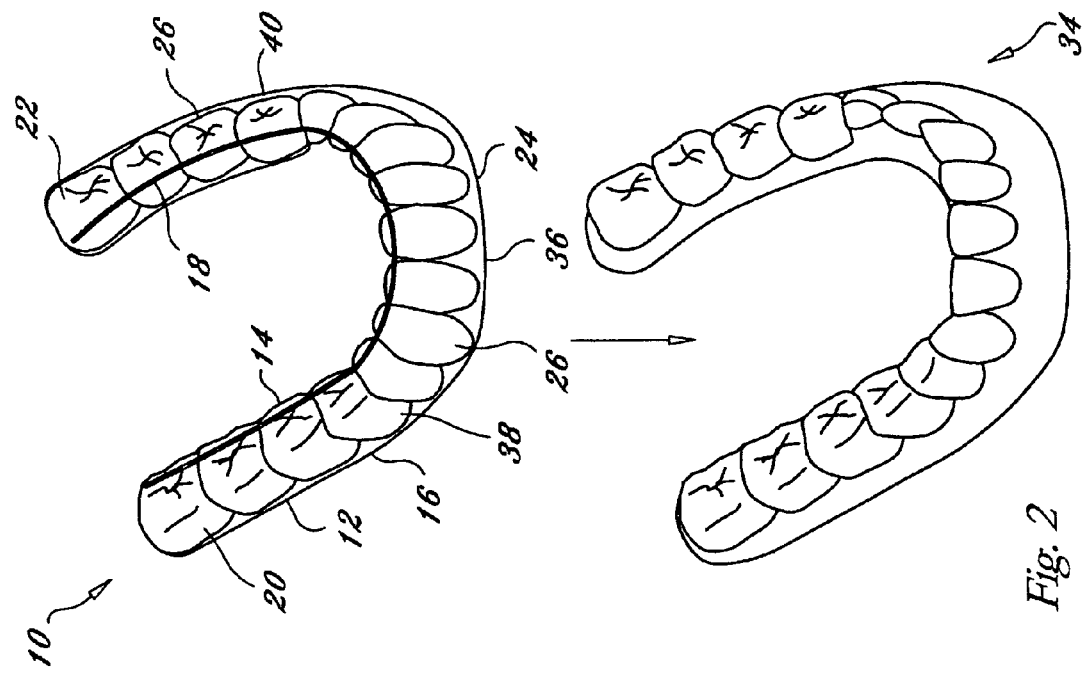
FIG. 2 is a perspective drawing of an alternative embodiment of the invention for the lower bridge of a patient.

An alternative embodiment is shown in FIGS. 2 and 2a. In Figures this embodiment, the appliance 10 comprise contours which cover the patient's teeth entirely. A second alternative embodiment is shown in FIG. 3. In FIG. 3, the appliance 10 covers the patient's teeth only from approximately the left molar to approximately the left canine and from approximately the right molar to approximately the right canine. As shown in FIG. 3, one wire 18 or a plurality of vertically parallel wires 18 are imbedded within the lingual side of the appliance 10. Such an appliance may be preferred in situations where the guidance of the plastic contours of the span 24 is not necessary, or where it is cosmetically advantageous for the patient to have no covering over the front teeth while the appliance 10 is worn.

Figure 6:
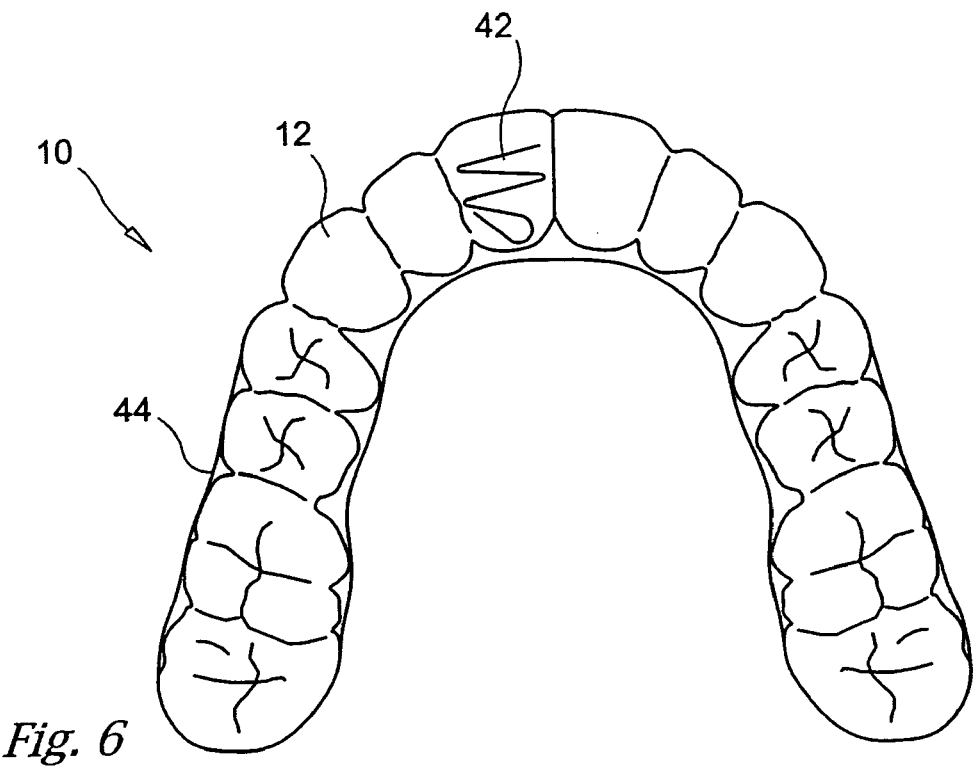
FIG. 6 is a top view of an embodiment of the invention for the lower bridge of a patient.
Figure 7:
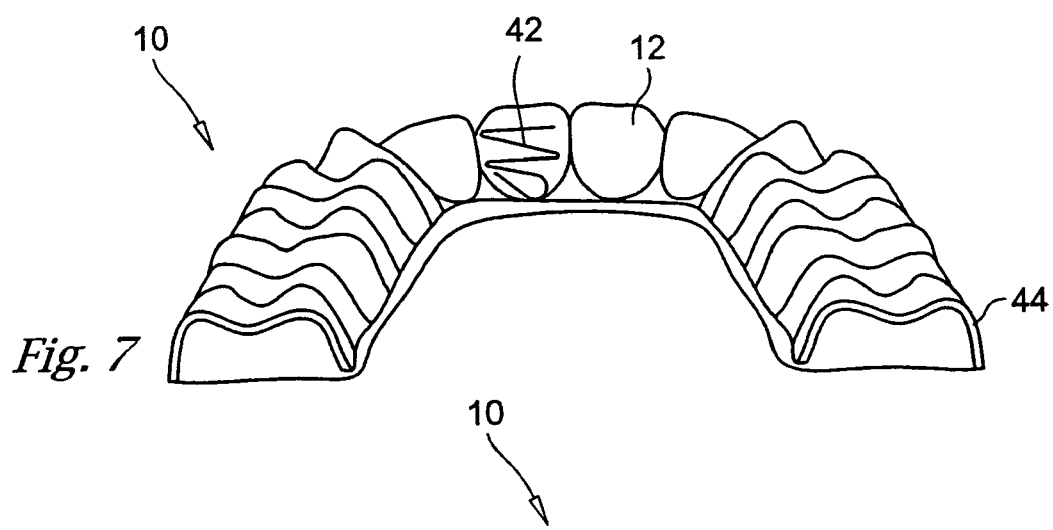
FIG. 7 is a back perspective view of an embodiment of the invention for the lower bridge of a patient.
Figure 8:
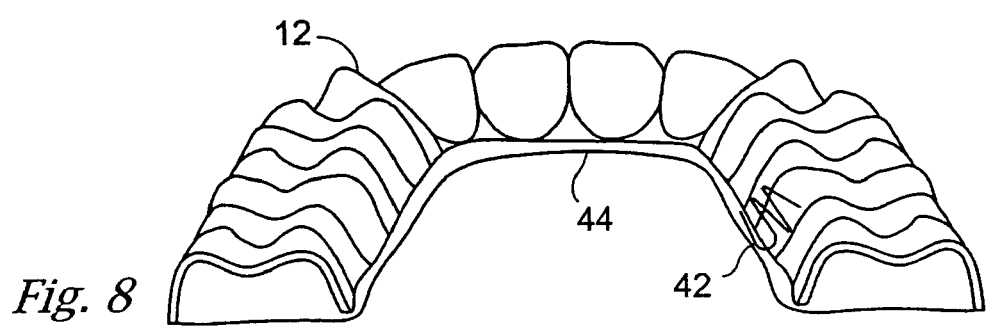
FIG. 8 is a back perspective view of a different embodiment of the invention for the lower bridge of a patient.

In another alternative embodiment, shown in FIGS. 6-8, the plastic portion 12 of the appliance 10 covers the entire surface of the patient's teeth from left molar to right molar, FIGS. 6-8 show this embodiment for a patient's lower bridge. One or more small fingers springs 42 are pre-fabricated and incorporated into the plastic portion during molding. The finger spring 42 may be located in the lingual side of the plastic portion 12, on the front teeth as shown in FIGS. 6-7 or on a molar as shown in FIG. 8. Alternatively, the finger spring may be located in the buccal side of the plastic portion. In addition, during the formation of the appliance 10, on the plaster model of the patient's bite used to make the appliance 10, the opposite side of the tooth 44 affected by the finger spring 44 may be built up with modeling clay to make a void in the appliance 10. The patient's tooth is then able to move into the void as pressure is applied to the tooth on the labial side by the finger spring 42. The use of the void allows selective movement of an individual tooth. However, several finger springs 42 may be used in this manner on a particular appliance 10. Finger springs 42 are preferably made of 0.014, 0.018 or rectangular wire, and are preferably made of stainless steel, nickel titanium alloy or an equivalent material.

The plastic structure 12 in this embodiment may also be the open structure as shown in FIGS. 1 and 3. Typical finger springs are made by Great Lakes Lab, Inc. or Pro Positioner, Inc.; however, they may also be made by hand. More or less pressure may be applied to a tooth by deforming the spring with pliers. Furthermore, the use of progressive springs on a tooth may be used on progressive appliances as described below.

The preferred method of forming the appliance 10 of this invention is as follows. A plaster cast of the patient's teeth and gums is taken by means already well known in the field of orthodontics. Then, appropriate plaster teeth are removed from the plaster cast of the gums, and reattached with modeling clay, floral arrangement putty or equivalent means to the plaster cast of the gums in a proper bite alignment. One or more wires or one or more finger springs are attached to the lingual surface of the plaster teeth using a means for attachment such as modeling clay or sculpting clay. The means for attachment must allow the wires to become imbedded within thermosetting plastic to be placed over the cast as described below. The cast of the properly aligned teeth is then put in a thermosetting plastic molding machine, preferably the Raintree Essix Amplified Vacuum Thermoforming Machine, or an equivalent compression vacuum machine. Also, a compression machine that operates on heated thermoplastic could also make the appliance, such as the compression machine made by Biostar, Inc. The appliance is then made by inserting thermosetting plastic in the compression vacuum machine or the compression machine. The thermosetting plastic is heated and flows around the cast of the aligned teeth and gums. Preferably, Essix C+ thermoplastic is used, although other plastics with equivalent physical properties are known in the art. The wires 18 are thus imbedded within the appliance 10 formed by the thermosetting plastic when the plastic cools. Preferably, the appliance 10 is removed from the machine and the lingual side of the appliance is trimmed to the general appearance of FIG. 1. However, the appliance may be untrimmed to provide the appliance as generally shown in FIG. 2 or trimmed to remove all thermoplastic from the front teeth, as shown in FIG. 3. Thus, when worn, the wire 18 will act as the pushing force on the patient's bite, while in the embodiments shown in FIGS. 1 and 2 the span 24 of the plastic portion 12 acts as a guide for the future placement of the patient's foremost teeth.

A series of appliances 10 with intermediate positions of the bite of the patient may be also formed. A series of appliances 10 may be preferred where complex movements are necessary to properly align the teeth of a patient. As above, the plaster teeth are removed from the plaster cast, and reattached to the plaster cast of the patient's gums with a material such as modeling clay, floral arrangement putty or the equivalent. However, the plaster teeth are serially reattached in one or more intermediate positions, and a plastic appliance is created from each of the intermediate positions.

Thus, when the appliances 10 are formed, the patient wears the appliances in series, and the patient's bite is progressively corrected until the final appliance 10 is used. The final appliance 10 properly aligns the patient's bite into proper alignment. Moreover, the wire or wires 18 in the intermediate appliances 10 may be varied as to number, thickness, shape and material to best and most quickly and efficiently alter the patient's bite at each intermediate step. This series would move faster than any series of appliances known in the prior art, because the imbedded wire would move the patient's teeth more rapidly than any plastic appliance in the prior art.

The preferred method for rapidly repositioning teeth from an initial arrangement to a final arrangement using a series of appliances as disclosed comprises of the following steps. A first incremental position adjustment appliance is placed over a patient's teeth, wherein the first appliance is plastic and has at least one wire imbedded within the lingual side of said first appliance to reposition the teeth from the initial tooth arrangement to a first intermediate arrangement. Then, one or more additional appliances are successively replaced on the patient, wherein the additional appliances each have at least one wire imbedded within the lingual side to rapidly reposition the teeth from the first intermediate arrangement to successive intermediate arrangements. Eventually, a final appliance is placed over a patient's teeth. Like the prior appliances, the final appliance has at least one wire imbedded within the lingual side of the first appliance to reposition the teeth and the final appliance positions the teeth from the last intermediate arrangement to a final tooth arrangement.

In one alternative embodiment, a plurality of vertically parallel wires is imbedded within the lingual side of the first appliance, the additional appliances and the final appliance. In other embodiments, the shapes of the wires utilized are of different shapes to better apply forces on the patient's teeth.

In another alternative embodiment, the invention is an expansion appliance with a spring such as a finger spring that that will distalize teeth, including molars.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A generally horseshoe shaped clear flexible resilient plastic wire-imbedded orthodontic appliance for an upper arch or a lower arch of a patient, comprising:
 a plastic portion with a lingual side, a labial side, a left molar area, a right molar area, a left canine area and a right canine area, including: contours on the lingual side and on the labial side, wherein the contours cover the patient's teeth so that the appliance remains in place over the patient's teeth and so that the plastic portion guides the force of one or more finger springs embedded within the lingual side of the plastic portion; and
 one or more individual wire finger springs completely embedded within the lingual side of the plastic portion, whereby the finger spring applies force on the lingual side of the patient's bite to rapidly correct the orientation of a tooth in the patient's bite.

2. The appliance of claim 1, wherein the plastic portion covers the surface of the patient's teeth from the left molar to the right molar.

3. The appliance of claim 1, wherein the plastic portion comprises a first outer section that covers the entire surface of the patient's teeth from approximately the left molars to the left canines, a second outer section that covers the entire surface of the patient's teeth from approximately the right molars to the fight canines, and the middle span that covers only the labial side of the patient's teeth approximately between the canines.

4. The appliance of claim 1, wherein the finger spring is fabricated from approximately 0.018 stainless steel wire.

* * * * *

UNITED STATES PATENT AND TRADEMARK OFFICE
CERTIFICATE OF CORRECTION

PATENT NO. : 7,416,407 B2  
APPLICATION NO. : 11/503591  
DATED : August 26, 2008  
INVENTOR(S) : Cronauer It is certified that error appears in the above-identified patent and that said Letters Patent is hereby corrected as shown below:

Column 1, line 43, after the word "Yousefian," delete "The" and add --the--.

Column 4, line 36, after the word "may" add --be--.

Column 4, line 44, after the word "extend" add --to--.

Column 5, line 2, after the word "Figures" add --2 and 2a of--.

Column 5, line 19, after the word "small" delete "fingers" and add --finger--.

Column 5, line 28, after the word "spring" delete "44" and add --42--.

Column 7, line 15, after the word "portion," add --said at least one finger spring each extending transversely to the horseshoe shape from a first end of the at least one finger spring to a second opposite end of the at least one finger spring, said individual wire finger springs being connected only to the plastic portion in which it is completely embedded,--.

Column 8, line 11, before the word "canines" delete "fight" and add --right--.

Signed and Sealed this

Twenty-third Day of December, 2008

JON W. DUDAS  
*Director of the United States Patent and Trademark Office*